United States Patent
Myrman et al.

(10) Patent No.: US 6,439,227 B1
(45) Date of Patent: Aug. 27, 2002

(54) BREATH-ACTUATION

(75) Inventors: Mattias Myrman, Stockholm (SE); Herbert Grässl, Schwandorf (DE)

(73) Assignee: Microdrug AG, Hergiswil (CH)

(*) Notice: Subject to any disclaimer, the term of this patent is extended or adjusted under 35 U.S.C. 154(b) by 0 days.

(21) Appl. No.: 09/686,087

(22) Filed: Oct. 12, 2000

(30) Foreign Application Priority Data

Sep. 25, 2000 (SE) .............................................. 0003409

(51) Int. Cl.$^7$ ............................................. A61M 11/00
(52) U.S. Cl. .............................. 128/200.14; 128/200.23
(58) Field of Search ....................... 128/200.14, 200.23, 128/203.15, 203.21

(56) References Cited

U.S. PATENT DOCUMENTS

| | | | |
|---|---|---|---|
| 3,456,646 A | * 7/1969 | Phillips et al. | 128/200.23 |
| 3,598,294 A | * 8/1971 | Hedrick et al. | 128/200.23 |
| 3,636,949 A | * 1/1972 | Kropp | 128/200.23 |
| 3,789,843 A | * 2/1974 | Armstrong et al. | 128/200.23 |
| 3,921,637 A | * 11/1975 | Bennie et al. | 128/203.15 |
| 5,031,610 A | * 7/1991 | Armstrong et al. | 128/200.23 |
| 5,119,806 A | * 6/1992 | Palson et al. | 128/200.23 |
| 5,217,004 A | * 6/1993 | Blasnik et al. | 128/200.23 |
| 5,392,768 A | * 2/1995 | Johansson et al. | 128/200.23 |

* cited by examiner

Primary Examiner—Aaron J. Lewis (74) Attorney, Agent, or Firm—Young & Thompson (57) ABSTRACT

An arrangement is disclosed for, in connection to an inhalation operation, opening and closing an air inlet of a dry powder inhaler device (DPI) provided with a pre-metered dosing member (4). The arrangement requires a certain well-defined minimum pressure differential between a surrounding atmosphere and the airways of the inhaling person to open the inlet for outside air to enter into the interior of the DPI. The arrangement controlling the opening and closing of the air inlet presents a biased flap connected to a biased catch mechanism. The biased flap (16) closes the air inlets (23) of the DPI to the atmosphere by the force exerted by a compression spring (13), which acts on the flap through a mechanism of levers. In order to open the flap a force $F_p$ bigger than the closing force $F_c$ of the spring and lever mechanism must be applied. The necessary force ensues from the pressure differential across the flap resulting when sucking the mouthpiece of the DPI to a certain degree. The catch is through the mechanism of levers released by the flap (16) when the flap opens, and triggers a sequence of events constituting the irreversible process of administering a dose to the user of the inhaler. The mechanism of levers connecting the flap, the spring and the catch uses rounded shapes (14) where moving parts are in contact with each other to minimize contact areas and rubbing effects and to achieve near zero friction losses. The flap is further provided with a counterweight (15) accomplishing the flap and the catch-mechanism to be statically and dynamically balanced, which almost completely eliminates the risk of external forces, e.g., gravitation or blows of the DPI to accidentally trigger the process of administering a dose.

9 Claims, 7 Drawing Sheets

BREATH-ACTUATION

TECHNICAL FIELD

The present invention relates to a breath-actuated administration of a dose of dry powder from a dry powder inhaler to a user, and more specifically the present invention relates to an arrangement for triggering off the process of delivering the dose to the user also involving opening and closing of an air inlet of a dry powder inhaler when subject to an inhalation operation.

BACKGROUND

Today supply and distribution of medical powders take place in many different ways. Within health care more and more is focussed on the possibility to dose and distribute powder directly to the lungs of a user by means of an inhaler to obtain an efficient, fast, and user-friendly administration of the specific medical substance.

Inhalers have been developed from being very simple to the up-to-date relatively complicated devices. For the up-to-date inhalers some form of mechanical dosing is almost entirely used for preparing the dose to be inhaled. Most often the dosing of the amount to be inhaled takes place industrially in advance in a dose package containing 5–50 doses. The inhaler then is loaded with this dose package as the source of each dose. Other inhalers have a magazine from which the powder is dosed by some device for distribution to the inspiration air. In both cases the powder will generally be strongly agglomerated and therefore must be dispersed.

There is a demand for arrangements improving and simplifying administration of medical powder by means of an inhaler providing a possibility to control the start of the inhalation airflow.

SUMMARY

The present invention discloses an arrangement for triggering off a process of administering a dose of dry powder, for instance a medical drug, by the breath of a person inhaling through a dry powder inhaler (DPI). The arrangement also controls the opening and closing of an air inlet in the inhaler. Particularly the arrangement according to the present invention is to be applied in a new continuous inhaler, i.e. an inhaler that controls the powder concentration and the time interval of the dose delivery to the user, thereby achieving a number of advantages in comparison to inhalers marketed today.

The present arrangement requires a certain well-defined minimum pressure differential between a surrounding atmosphere and the airways of the inhaling person to trigger off the process of delivering the dose and to open an inlet for outside air to enter into the interior of the DPI. The arrangement controlling the triggering mechanism and the opening and closing of the inlet of air into the DPI presents a flap connected to a biased catch mechanism. The flap closes the air inlet of the DPI to the atmosphere by the force exerted by a spring, which acts on the flap through a mechanism of levers. In order to open the flap a force bigger than the closing force of the spring and lever mechanism must be applied. The necessary force ensues from the pressure differential across the flap resulting when the user sucks through the mouthpiece of the DPI to a certain degree. The catch is through the mechanism of levers released by the flap when the flap opens, and triggers a sequence of events constituting the irreversible process of administering a dose to the user upon his or hers inhalation through the inhaler.

The mechanism of levers connecting the flap, the spring and the catch uses rounded shapes where moving parts are in contact with each other to minimize contact areas and rubbing effects and to achieve near zero friction losses. The biased flap is further provided with a counterweight accomplishing the flap and the catch-mechanism to be statically and dynamically balanced, which almost completely eliminates the risk that external forces, e.g., force of inertia, gravitation or blows to the DPI accidentally will trigger the process of administering a dose if, for instance, the device should be dropped.

DESCRIPTION OF THE DRAWINGS

The invention will be described in the form of a preferred and illustrative embodiment and by means of the attached drawings wherein like reference numbers indicate like or corresponding elements and wherein.

DESCRIPTION OF AN ILLUSTRATIVE EMBODIMENT

Figure 1:
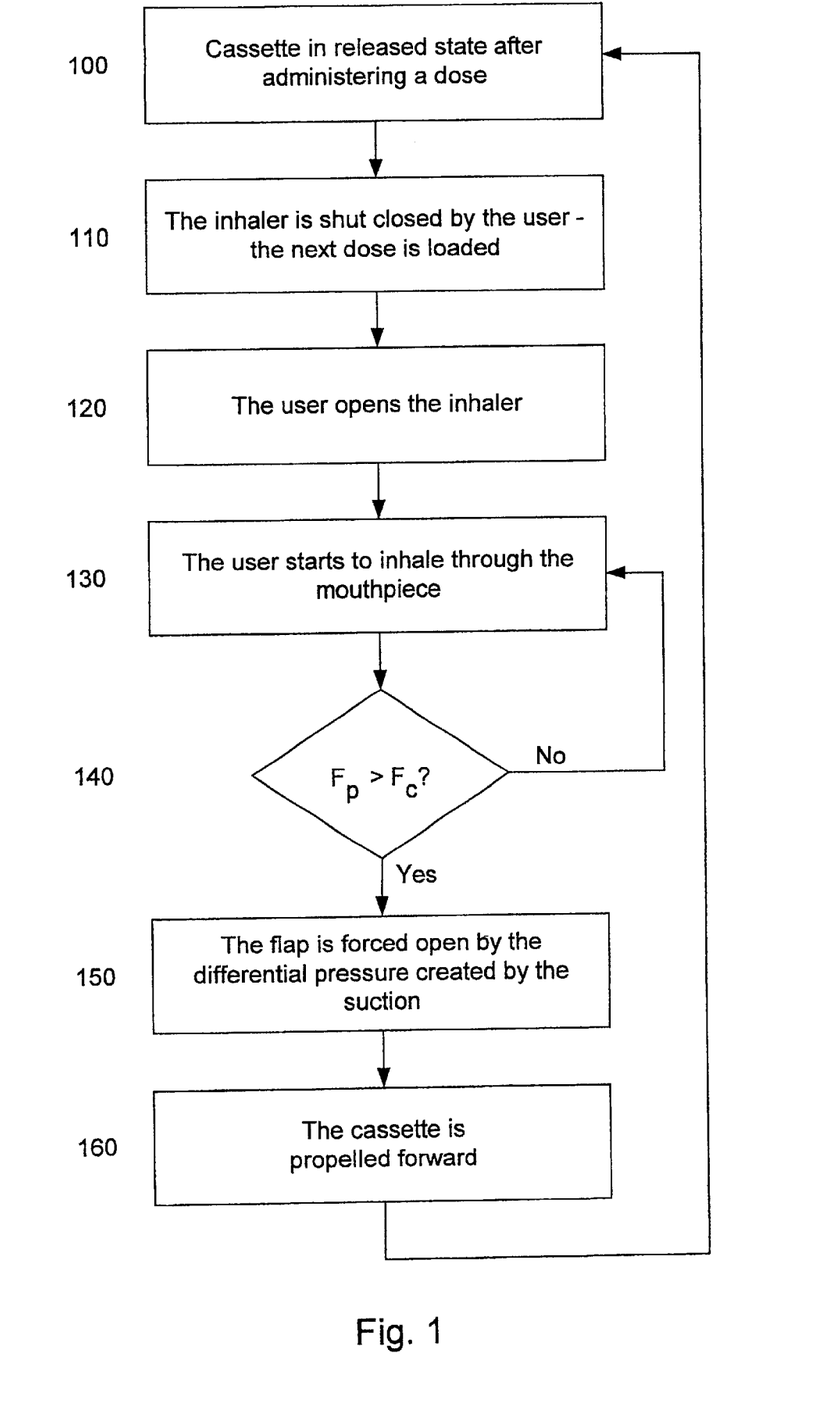
FIG. 1 illustrates a flow chart of a complete cycle of operating the dry powder inhaler with respect to the arrangement of the present invention.

FIG. 1 describes a complete cycle of operating an illustrative dry powder inhaler, DPI, by illustrating in a flow chart the actions performed by a user and the events these actions give rise to. Taking reference in the flow chart the operation of the present invention is illustrated.

Figure 3:
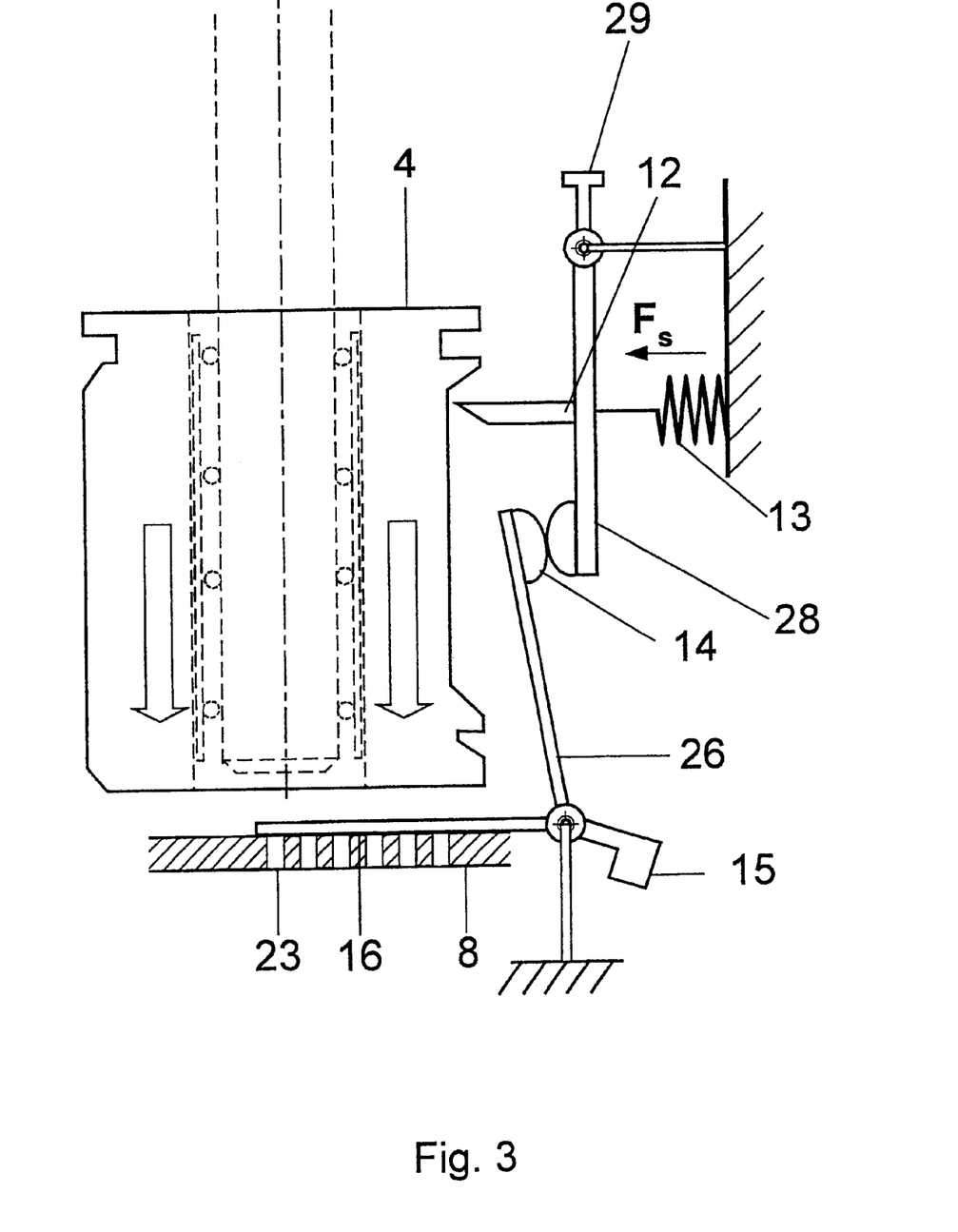
FIG. 3 illustrates an embodiment of the internals of the inhaler, with a dosing cassette, a flap, a spring and a catch mechanism after an inhalation operation has ended.

The starting point in FIG. 1 is step 100, i.e., the DPI is in the open state where the DPI has delivered a dose to the user, who has stopped inhaling, which is also schematically illustrated in FIG. 3. A movable dosing member 4, carrying one or more pre-metered doses, is in the released state and a biased flap 16 is in the closed position, stopping air from entering the DPI through the air inlet, illustrated as vent holes 23. In a preferred embodiment the pre-metered dosing member 4 is a replaceable cassette containing a number of enclosed pre-metered doses of powder for inhalation purposes.

Figure 4:
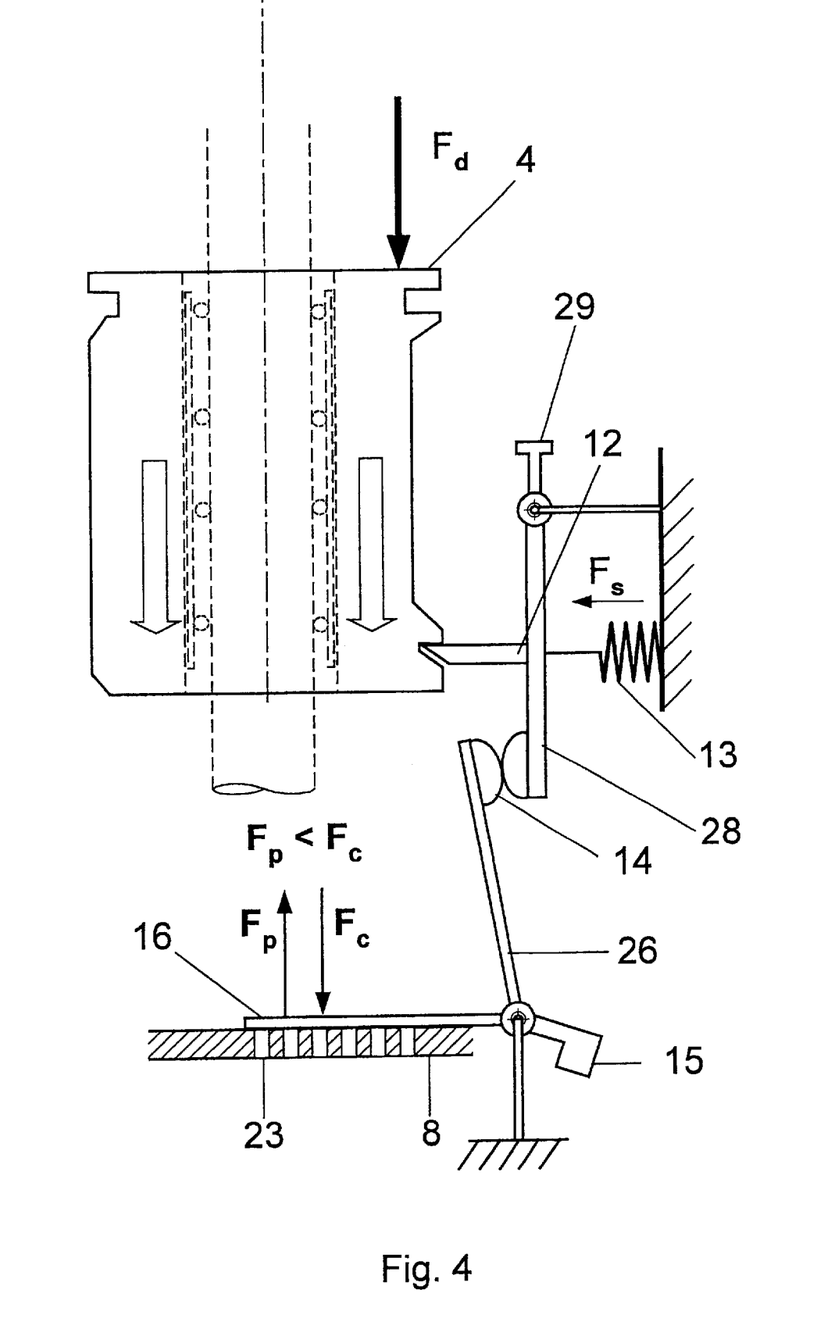
FIG. 4 illustrates the embodiment of the internals of the inhaler, with the dosing cassette, the flap, the spring and the catch mechanism prior to an inhalation operation.

In the next step 110 the DPI is put into the closed state, schematically illustrated in FIG. 4. The cassette 4 is pushed back, sliding like a sleeve on a pillar, by the closing action performed by the user and brought in a position for delivering a next dose. When the DPI is closed a drive spring (not illustrated) is tensed, acting on the cassette 4, which is secured in this position by a plunger element (not illustrated). The catch 12 of the flap mechanism is forced into a mating notch in the cassette by the compression spring 13, thereby also locking the cassette 4 in a ready position.

When the user according to step 120 then again opens the DPI to get access to the mouthpiece (not illustrated), the plunger element mentioned before is removed leaving only the catch 12 to hold the cassette 4 in position, ready to deliver a dose.

As the user, in step 130, starts to inhale the flap 16 remains shut preventing air to flow into the inhaler and consequently the cassette 4 remains in its initial position until the pressure differential induced by the user's sucking creates an opening force $F_p$ on the flap 16 that is big enough to counteract the closing force $F_c$. $F_c$ is the resulting force on the flap of force $F_s$ from the compression spring 13, acting through the levers 28 to keep the flap 16 closed. The forces acting on the flap 16 directly and indirectly are summarized and compared in step 140.

Figure 5:
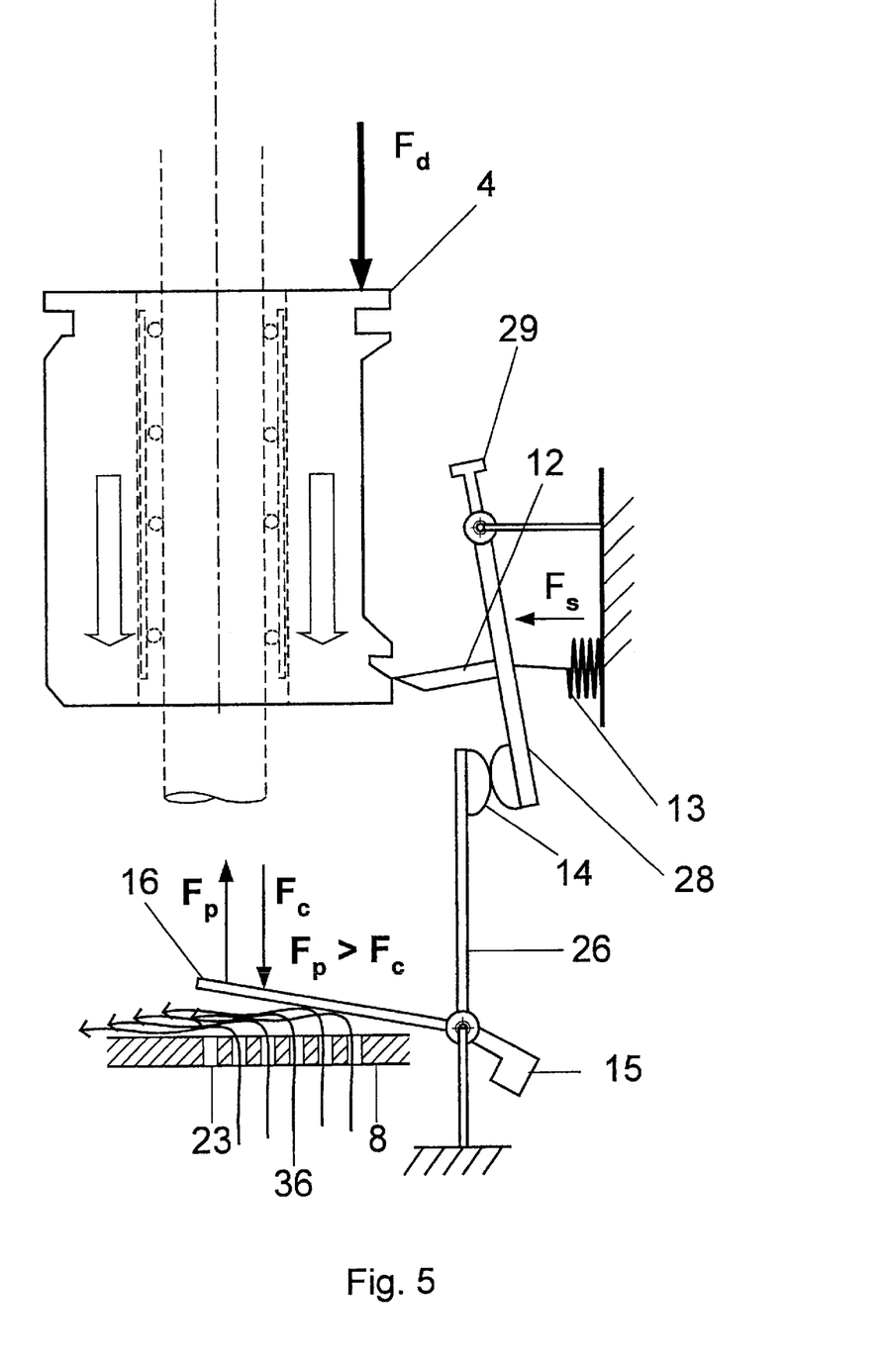
FIG. 5 illustrates the embodiment of the internals of the inhaler, with the dosing cassette, the flap, the spring and the catch mechanism, the moment after the inhalation by the user has begun.

As soon as the user's suction is strong enough, which from the user's point of view is felt to be immediately after the inhalation begins, in step 150, the biased flap 16 is forced open, the catch 12 releases the cassette 4 so that it can be pushed forward by its drive spring (not illustrated) acting on the cassette with force $F_d$. This condition is schematically illustrated in FIG. 5.

Figure 6:
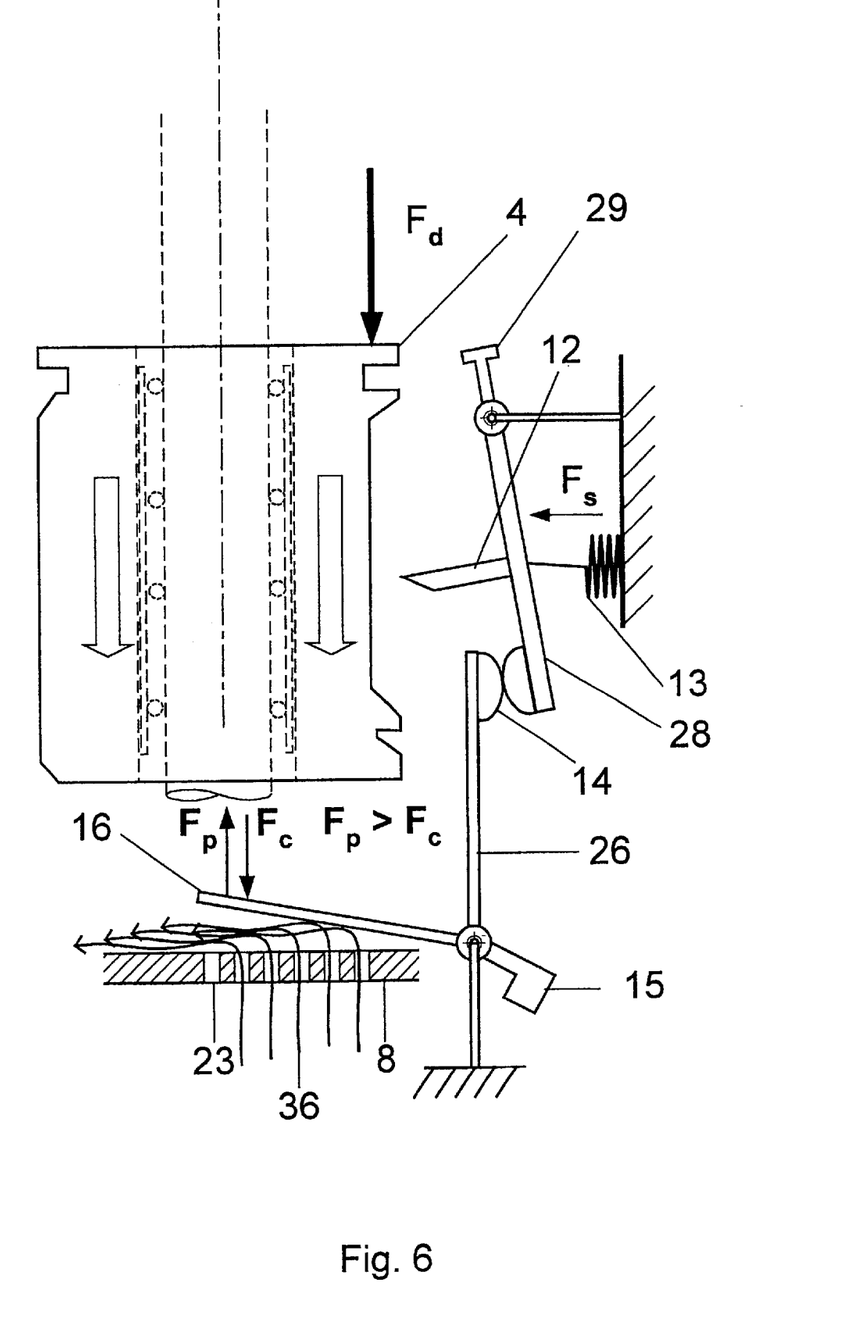
FIG. 6 illustrates a principal sketch of the internals of the inhaler, with the dosing cassette, the flap, the spring and the catch mechanism, a few moments after the inhalation has started and the cassette is in motion.

In step 160 the cassette 4, now free to move, is propelled forward as schematically illustrated in FIG. 6, at constant or variable speed as the case may be, with the object of delivering the dose continuously to the user. The air now inhaled picks up the powder of the pre-metered dose from the cassette 4 and brings the powder into the user's airways, lungs or deep lungs or a combination thereof depending on what is the overall objective for the inhalation.

Figure 2:
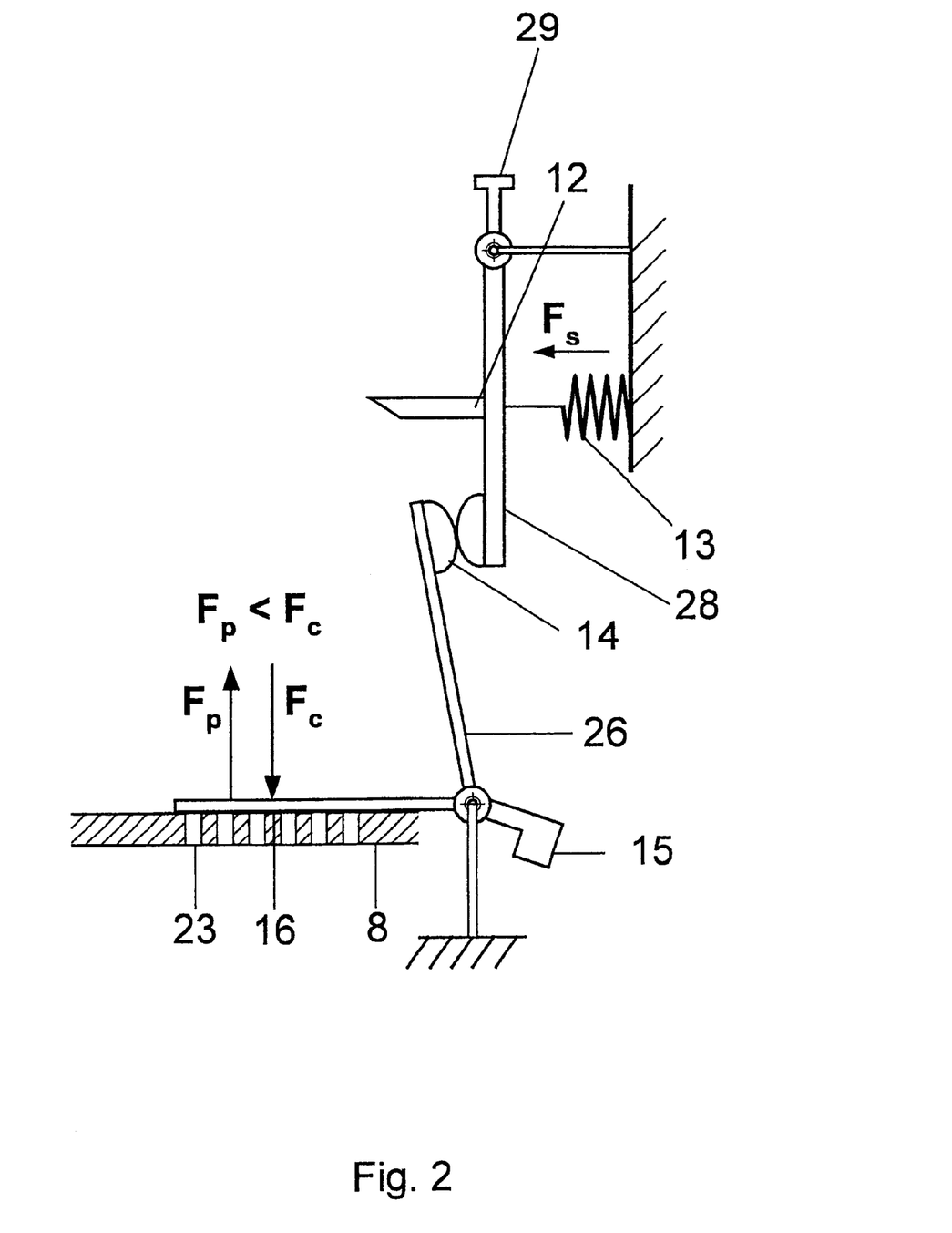
FIG. 2 illustrates a principal sketch of the biased flap and catch mechanism.

An illustrative embodiment of the invention is disclosed in FIG. 2. The inlet of air into the body wall 8 of the DPI is illustrated as a number of vent holes 23, but the inlet can be realized in different ways in additional embodiments of the invention. If necessary to stop the ingress of dirt etc into the DPI a fine mesh filter (not illustrated) can be affixed to the air inlet. The flap 16 is pivoted in the body of the DPI preferably using low friction materials and arranged to minimize friction so that the flap can move freely. The flap 16 is fixed to a lever 26 as is further illustrated by FIG. 7. The flap 16 in FIG. 2 is pushed tightly against the inside of the DPI body wall 8 by the force given by the compression spring 13, which is acting on the flap 16 through the lever 28 over the rounded means 14 and through lever 26. The flap and the inner surface of the DPI body are preferably made such that the flap in the closed position effectively closes the inlet of air 23 into the DPI with as little leakage as possible. The lever 28 is pivoted in the body of the DPI preferably using low friction materials and arranged to minimize friction so that the lever can move freely.

When the user begins to inhale through the mouthpiece (not illustrated) of the DPI the suction results in a building up of a pressure differential between the surrounding atmosphere and the airways of the user, such that the local pressure in the airways of the subject is lower than the atmospheric pressure. Since the flap 16 is closed at this stage air cannot flow through the vent holes 23 into the DPI, through the mouthpiece and into the mouth of is the user. Depending on the efficiency of the flap 16 there is almost no flow of air past the flap, so that almost the full pressure differential is present across the front and back of the flap, which results in a force acting on the flap counteracting the closing force of the spring 13.

When the differential pressure is big enough the resulting force $F_p$ acting to open the flap overcomes the closing force $F_c$ resulting from the spring force $F_s$ acting through the lever system 28 and 26 so that the flap opens and lets air 36 into the DPI. By using a different spring 13 with a different rate or changing the positions of the pivot points 27 and 25 for the levers 28 and 26 or by using a different lever geometry, or a combination of these methods, it is possible to adjust the closing force acting on the flap. In this way the required minimum force $F_p = F_{minimum}$ to open the flap can easily be chosen to suit the particular DPI and serve the objectives of the DPI to the best advantage.

When the inhalation opens the flap the opening force acts through the lever 26 over the rounded surfaces 14 onto lever 28 and compresses the spring 13. The induced movement of lever 28 withdraws the catch 12, which is fixed to the lever, from its locking position. Then the cassette 4 held by the catch is made free to move, which is also indicated by FIG. 5, where this state is schematically illustrated. By subsequently controlling the motion of the released cassette 4 the administration of the pre-metered dose will be controlled in an appropriate manner.

Figure 7:
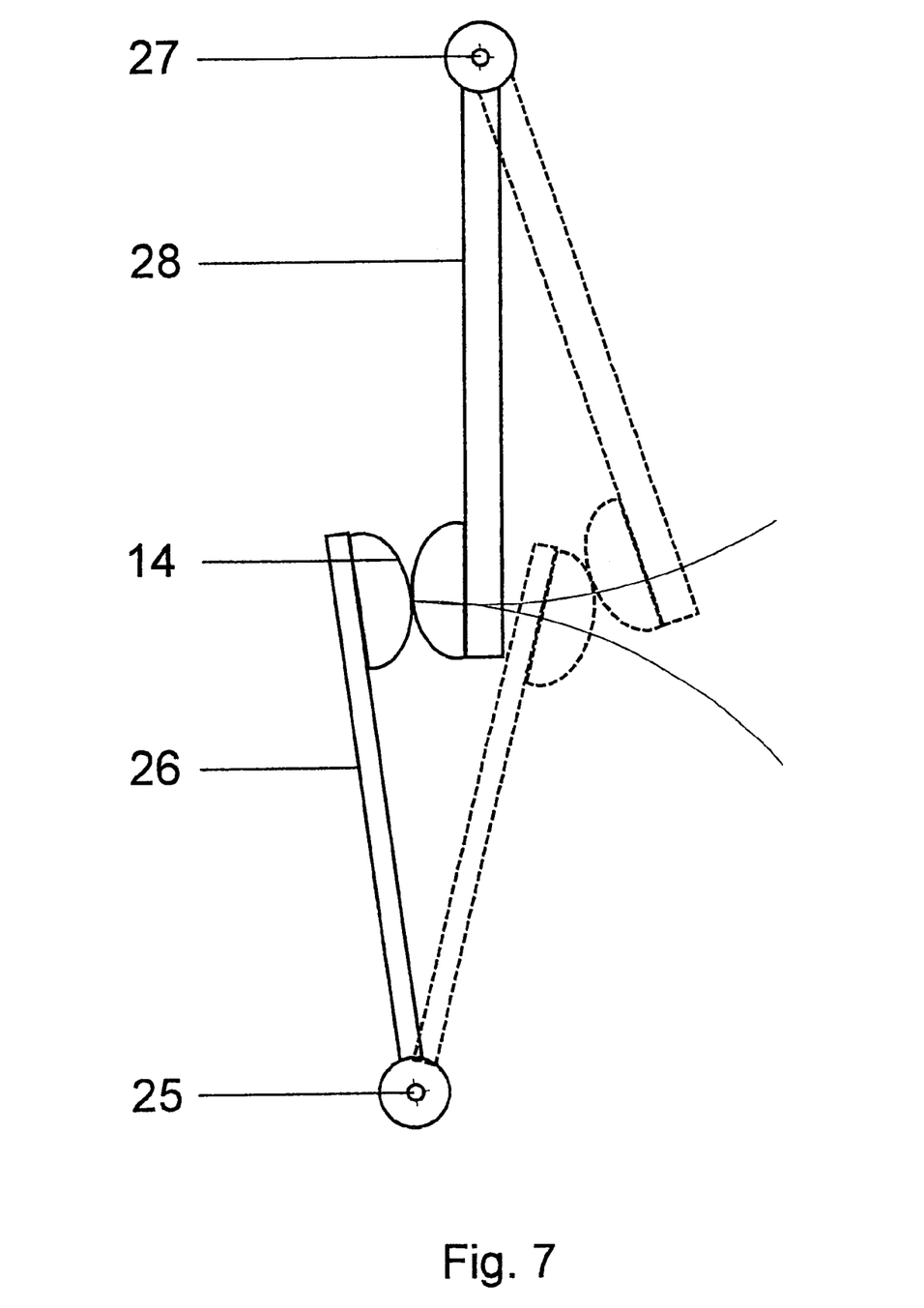
FIG. 7 illustrates a principal sketch of how the rounded surfaces interact.

In FIG. 7 the rounded contact area 14 is disclosed in more detail. The rounded shapes of the contact area contribute strongly to the efficiency of the arrangement according to the present invention by transmitting power from lever 26 to lever 28 or vice versa almost without friction loss. The inevitable relative movement between the levers is not a rubbing action but a rolling action such that the point of contact moves like two cogs meshed in a gear wheel, resulting in very low friction loss. Preferably the materials and surface qualities of the rounded surfaces 14 are selected to further reduce friction and power loss in the materials.

The illustrative embodiment of the invention in FIG. 2 shows a counterweight 15 fixed to the same member as the flap 16 and the lever 26. Its construction and position relative the flap and the lever are such that it balances the masses of the flap and the lever statically as well as dynamically, so that the center of gravity is in the center of the pivot. This will minimize the risk of forces of inertia, acting on the triggering mechanism, unintentionally activating the dose delivery process, e.g. if the DPI is dropped.

Another counterweight 29, which is fixed to the same member as the lever 28, is fitted if necessary to balance the lever 28 in the same manner as described for the counterweight 15.

It will be understood by those skilled in the art that various modifications and changes may be made to the present invention without departure from the scope thereof, which is defined by the appended claims.

What is claimed is:

1. A breath-actuation arrangement for an inhaler, initiating a delivery of a pre-metered dose of medication powder by opening and closing an air inlet of a dry powder inhaler device having a pre-metered dosing member, the arrangement comprising:

a means for releasing a pre-metered dosing member;

a biased flap actuating said means for releasing said biased flap being movable from an open position to a closed position; and a joint having very low friction los s connecting the biased flap and the releasing means;

said biased flap opening when a user inhaling through a mouthpiece of an inhaler device exerts an air suction exceeding a threshold value counteracting an exerted force $F_c$ acting on the releasing means, said biased flap closing an air inlet of a dry powder inhaler when an air suction of a user is less than the threshold value air inlet.

2. The arrangement according to claim 1, wherein said joint connects a first end of a first lever to a first end of a second lever, a second end of said first lever being attached to said biased flap at a pivoting center, said second lever is connected to the releasing means and is pivoted at a second end, the exerted force $F_c$ forces said second lever to move the releasing means to lock said pre-metered dosing member, said second lever acting on said first lever to force said biased flap to the closed position.

3. The arrangement according to claim 2, wherein said joint is two rounded members making a point contact and in motion presents a low friction contact.

4. The arrangement according to claim 3, wherein at least one of said first and second levers further comprise, at an end opposite to said joint, a counterweight for statically and dynamically balancing the masses of the biased flap and the first and second levers.

5. The arrangement according to claim 1, wherein said biased flap in the closed position covers at least one inlet opening of an inhaler body wall to make an inhaler body wall airtight.

6. A breath-actuation arrangement for an inhaler, initiating a delivery of a pre-metered dose of a medication powder by opening and closing an air inlet of a dry powder inhaler device having a pre-metered dosing member, the arrangement comprising:

a means for releasing a pre-metered dosing member;

a biased flap actuating said means for releasing;

a low friction joint connecting said biased flap to said means for releasing, wherein when a user exerts an air suction exceeding a threshold value counteracting an exerted force $F_c$ acting on the releasing means, said biased flap opens an air inlet and said releasing means releases a pre-metered dosing member, and wherein said joint is between a first end of first and second levers, said first lever having a second end attached to said biased flap at a pivoting center, said second lever being connected to said releasing means, a second end of said second lever being pivotable, the exerted force $F_c$ forcing said second lever to move the releasing means to lock said pre-metered dosing member, said second lever being adapted to move said first lever to force said biased flap to a closed position.

7. The arrangement according to claim 6, wherein said joint is first and second rounded members at said first ends of said first and second levers, said first and second rounded members defining a single contact point to present a low friction contact.

8. The arrangement according to claim 7, wherein one of said first and second levers further comprise at an end opposite to said joint, a counterweight for statically and dynamically balancing the masses of the biased flap and levers of the arrangement.

9. A breath-actuation arrangement for an inhaler, initiating a delivery of a pre-metered dose of a medication powder by opening and closing an air inlet of a dry powder inhaler device having a pre-metered dosing member, the arrangement comprising:

a means for releasing a pre-metered dosing member;

a biased flap actuating said means for releasing;

a low friction joint connecting said biased flap to said means for releasing, said biased flap being movable from a first position to close an air inlet of a dry powder inhaler device, to a second position to open an air inlet of a dry powder inhaler device, by a user exerting an air suction that exceeds a threshold value for counteracting an exerted force $F_c$ acting on said releasing means, said biased flap automatically moving back to the first position when a user stops exerting an air suction that exceeds a threshold value for counteracting an exerted force $F_c$ acting on said releasing means.

* * * * *